United States Patent [19]

Dixon

[11] 4,189,463
[45] Feb. 19, 1980

[54] IMMUNOASSAY FOR ZOXAZOLAMINE

[75] Inventor: William R. Dixon, Dumont, N.J.

[73] Assignee: Hoffmann-La Roche Inc., Nutley, N.J.

[21] Appl. No.: 894,280

[22] Filed: Apr. 7, 1978

[51] Int. Cl.$^2$ ............... G01N 33/16; A61K 39/00; A61B 10/00

[52] U.S. Cl. .................................. 424/1; 23/230 B; 260/112 B; 424/12

[58] Field of Search ............... 424/1, 12; 23/230 B; 260/112 B

[56]  References Cited
PUBLICATIONS

Conney et al., Fed. Proc., vol. 36, No. 5, Apr. 1977, pp. 1647–1652.

Primary Examiner—Benjamin R. Padgett
Assistant Examiner—Christine M. Nucker
Attorney, Agent, or Firm—Jon S. Saxe; George M. Gould

[57] ABSTRACT

The preparation of immunogens and selective antibodies for zoxazolamine therefrom as well as an immunoassay for zoxazolamine using said antibodies is described. Such immunoassay can be utilized to determine an individual's zoxazolamine half-life which has been correlated with the genetically controlled level of benzo[a]pyrene hydroxylase induction. The latter measurement has been associated with risk to carcinoma. Thus, determination of the zoxazolamine half-life by means of the instant immunoassay can be used as a screening test for identifying individuals at special risk to cancer.

6 Claims, No Drawings

IMMUNOASSAY FOR ZOXAZOLAMINE

BACKGROUND OF THE INVENTION

In view of our increasing awareness that environmental carcinogens, such as polycyclic aromatic hydrocarbons, aflatoxins and nitrosamines, may be responsible for the production of certain cancers in man, it would be desirable to have a simple screening procedure to identify those individuals who are at an unusually high risk when exposed to such carcinogens and/or other environmental pollutants. Kapitulnik et al., Clin. Pharmacol. Therap. 20, 557 (1976) have suggested that such screening might be possible by determining the plasma half-life of drug which is metabolized by the same enzyme system(s) that metabolizes the environmental pollutant. One such drug which might serve this purpose is zoxazolamine (2-amino-5-chlorobenzoxazole). Kapitulnik et al., supra, have recently demonstrated that there is a highly significant correlation ($r=0.98$:$p <0.001$) between the hydroxylation of benzo[a]pyrene (BP), a known carcinogen, and zoxazolamine in the placentas from smokers and non-smokers which suggests that BP and zoxazolamine are metabolized in the human placenta by the same enzyme system or by different systems which are under similar regulatory control. A somewhat weaker relationship has been found between BP and zoxazolamine metabolism in the human liver, Kapitulnik et al., Clin. Pharmacol. Therap. 21, 166 (1977). Furthermore, Kellerman et al., Am. J. Hum. Genet. 25, 327 (1973), using human lymphocytes, have shown a positive correlation between the occurrence of bronchogenic carcinoma and an individual's capacity to metabolize BP.

With these facts in mind, a simple and rapid method is required for the determination of the plasma half-life of zoxazolamine if the latter is to be used as a screening procedure in the general population. The technique of immunoassay, particularly radioimmunoassay (RIA), by virtue of its simplicity, would satisfy this requirement.

U.S. Pat. No. 3,988,430 discloses a radioimmunoassay for antipyrine whose half-life in a subject has been correlated with the genetically controlled level of benzo[a]pyrene hydroxylase induction. The latter measurement has been associated with risk to bronchogenic carcinoma.

DESCRIPTION OF THE INVENTION

The present invention relates to an immunoassay, particularly a radioimmunoassay for zoxazolamine employing novel antibodies which are selective for this compound and to novel immunogens useful in eliciting the aforesaid antibodies. Such radioimmunoassay is far more sensitive than the presently employed spectrophotometric technique for assaying for zoxazolamine and yet is still a relatively simple and rapid procedure. Moreover, the assay of the present invention can be employed on unextracted plasma samples thereby making it a convenient procedure even in commercial laboratories.

The immunoassay employed in the present invention comprises zoxazolamine covalently bonded through a suitable linking group to a conventional immunogenic carrier material. As used herein the term "immunogenic carrier material" is meant to include those materials which have the property of independently eliciting an immunogenic response in a host animal and which can be covalently coupled to the zoxazolamine hapten. Suitable carrier materials include, for example, proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. Bovine serum albumin is a preferred protein material. Other suitable protein materials will be suggested to one skilled in the art. It is generally preferred but not critically necessary that protein materials be utilized which are foreign to the animal hosts in which the resulting antigen will be employed.

It is desirable to modify the structure of zoxazolamine by introducing a suitable linking group which can serve to couple the zoxazolamine to the immunogenic carrier material. Thus, for example, zoxazolamine may be reacted with a p-nitrobenzoyl halide, e.g., p-nitrobenzoyl chloride. The resulting nitrobenzamide product may then be reduced with either hydrogen in the presence of a noble metal catalyst such as palladium on charcoal or chemically by use of a metal, e.g., iron, tin or zinc in an acid solution in a manner known per se.

The resulting p-phenylamine derivative of zoxazolamine can then be diazotized and coupled to the immunogenic carrier material by procedures well known in the art. Thus, an aqueous solution of the diazonium salt can be added slowly to an aqueous solution of the carrier material at a temperature in the range of from about 0° to 4° C. until the reaction is completed, i.e., from 4 to 16 hours. The coupled product is isolated by dialysis and then lyophilized.

The zoxazolamine immunogen hereinabove described may be utilized to induce formation of antibodies specific to zoxazolamine in host animals by injecting the antigen in such a host animal, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with zoxazolamine.

The antibodies of the present invention are useful as reagents for the determination of zoxazolamine concentration in biological fluids, preferably plasma. In one useful assay procedure, a known amount of labelled zoxazolamine is mixed with the above antibody and a sample containing zoxazolamine is added. The amount of zoxazolamine in the sample can be determined by measuring the inhibition of the binding to the zoxazolamine antibody of the labelled zoxazolamine by the sample and comparing the value observed with a standard curve previously developed. The reagents may be added in any order. A suitable assay procedure of this purpose is described in greater detail in U.S. Pat. No. 3,709,868.

Suitable labelled zoxazolamines for assay purposes include radioisotopically labelled zoxazolamine, particularly labelled with tritium ($^3H$), carbon 14 ($^{14}C$) or with iodine 125 ($^{125}I$). One may also employ zoxazolamine labelled with any other unique and detectable label such as for example an electron spin resonance group. Examples of the use of various electron spin resonance labelled molecules in bioassays are to be found in U.S. Pat. Nos. 3,453,288, 3,481,952 and 3,507,876. Other suitable labels include chromophores, fluorophors, enzymes, red blood cells, latex particles, etc.

EXAMPLE

Materials and Methods

Assay buffer: The assay was carried out using 0.01 M phosphate buffered saline (PBS) at pH 7.4 containing 0.1% bovine gamma globulin and 0.1% sodium azide.

Radioligand: 4,6-$^3$H-zoxazolamine (1.06 Ci/mM) was prepared essentially as described by Tomaszewski et al., Arch. Biochem. Biophys. 176, 788 (1976) with the following modifications in order to produce material of much higher specific activity:

Phosphorus pentachloride (4.5 mg.) was decomposed with 0.1 ml. of water and to the resulting solution 12 mg. of 2-amino-4-chlorophenol was added. The entire solution was then transferred to a reaction vessel having a high vacuum stopcock and a total capacity of 0.5 ml. After this apparatus was attached to a vacuum line and the solution de-gassed (freeze/thaw), 0.04 ml. of tritium oxide (20 Ci; 10 Ci/mmol) was introduced by vacuum transfer (liquid nitrogen). The reaction vessel was then sealed and the solution allowed to come to room temperature. Equilibration was then carried out as previously described by Tomaszewski et al., supra. The purified product was stored in toluene at $-20°$.

$^3$H-zoxazolamine was dissolved in assay buffer at a concentration of 150,000 dpm/ml for use in the RIA.

Synthesis of hapten: Zoxazolamine (1.54 g.) was dissolved in a mixture of dry methylene chloride (100 ml.), tetrahydrofuran (8 ml.) and pyridine (3 ml.) to which p-nitrobenzoyl chloride (2.04 g.) was added. The solution was stirred at room temperature for 8 hours during which time the product precipitated from the medium as a light yellow solid. Two recrystallizations from acetone provided 1.7 g. of light yellow needles (m.p. 247°-249°) of pure 4-nitro-N-(5-chloro-2-benzoxazolyl)-benzamide $C_{14}H_8O_4N_3Cl$,

| % calculated | C | 52.93 | % Found | 52.95 |
|---|---|---|---|---|
| | H | 2.54 | | 2.45 |
| | N | 13.23 | | 13.29 |
| | Cl | 11.16 | | 11.23 |

This amide readily sublimes above 200°.

The nitro derivative (300 mg.) was quantitively reduced to 4-amino-N-(5-chloro-2-benzoxazolyl)benzamide by stirring with 50 mg. of 10% palladium on carbon in 50 ml. of tetrahydrofuran and 2.5 ml. of acetic acid under 2 atmospheres of hydrogen for 2 hours. The catalyst was removed by filtration and the solution was concentrated to a tan solid. Since the amine darkens on attempted recrystallization, presumably due to autoxidation, it was used as such in further reactions. Both the nitro and amino derivatives gave acceptable nmr and mass spectra and were homogeneous on TLC. Combustion analysis of the crude amino derivative (m.p. 202°-204°) gave acceptable values for H, N, and Cl, but was 0.98% low for carbon.

Preparation of Immunogen: The hapten, 4-amino-N-(5-chloro-2-benzoxazolyl)benzamide (27 mg., 0.1 mM) was dissolved in N,N-dimethylformamide (2 ml.) containing water (0.2 ml) and the solution treated with 1 N HCl (0.4 ml). After cooling to 4°, a 1 M aqueous solution of sodium nitrite (0.095 ml.) was added with stirring to give a bright yellow solution of the diazonium salt of the hapten. After 30 minutes at 4° any excess of nitrous acid was decomposed by the addition of 1 M aqueous ammonium sulfamate (0.03 ml.) and continuous stirring for an additional 5 minutes. The diazonium salt was then added dropwise with stirring to a solution of bovine serum albumin (70 mg., 1 µM) in 5 ml. of 0.16 M borate buffer (pH 9) at 4°. A dark solution resulted which was stirred at 4° for 2 hours and then dialyzed against 0.01 M Tris buffer (pH 8) in the dark at room temperature. Exhaustive dialysis was continued against isotonic saline followed by water. The diazo conjugate of the hapten and bovine serum albumin (immunogen) was isolated as a dark-orange fluffy powder following lyophilization. During all of the previously outlined dialysis procedures, no visably noticeable colored material was released from the dialysis bag which indicated that extensive covalent diazo coupling of the hapten to the albumin had been achieved.

Immunization Schedule and Production of Antisera: Four New Zealand White Rabbits (2 males, No. 94 and 95 and 2 females, No. 96 and 97) were each immunized by intradermal injection of a total of 0.5 mg. of the immunogen as an emulsion in Freund's complete adjuvant at 6 sites on the back. The immunization procedure was repeated using freshly prepared emulsion at 2 weeks and 4 weeks following the initial immunization. Then at monthly intervals each animal was given a booster immunization by intravenous and subcutaneous injection of 200 µg of immunogen as a solution in isotonic saline via both routes (400 µg total) and bled from the central ear artery 7-10 days later. Serum was harvested and stored at $-20°$.

Antiserum Characterization: Titer was defined as the final dilution of antiserum which bound 50% of the radioligand, $^3$H-zoxazolamine, and was determined in the following manner:

Each lot of antiserum was serially diluted with PBS and 0.1 ml. aliquots added to 12×75 mm glass assay tubes. Then 0.1 ml. (15,000 dpm) of the stock solution of $^3$H-zoxazolamine was added and the volume adjusted to 0.5 ml. with PBS. The contents of each tube were mixed and allowed to incubate at room temperature for 30 minutes. The antibody-bound radioligand was precipitated by the addition of an equal volume (0.5 ml.) of saturated ammonium sulfate (pH 7.4), the tube contents were mixed and centrifuged at 5000 rpm for 30 minutes at 4°. The supernate was removed by aspiration and the precipitate (antibody-bound radioligand) washed with 1 ml. of 50% saturated ammonium sulfate. Following repetition of the centrifugation and aspiration procedures, the washed precipitate was dissolved in 0.4 ml. of water, 3 ml. of Aquasol ® (New England Nuclear, Boston, Massachusetts) added, the contents mixed immediately and the tube capped with a size 5X Caplug ® (Protective Closures Inc., Buffalo, New York). The samples were then counted in a modified liquid scintillation counter as described by Dixon and Cohen, Clin. Chem. 22, 1746 (1976). All determinations were carried out in duplicate and the extent of antibody-binding expressed as a percentage of the total counts of $^3$H-zoxazolamine added after correction for non-specific binding of the radioligand in the absence of antiserum.

Calibration curves for zoxazolamine were generated by adding known amounts of the unlabelled drug in 0.1 ml. of PBS to tubes containing a constant amount of suitably diluted antiserum (50% binding of the $^3$H-zoxazolamine) and tracer. Calibration curves were also generated in the presence of 50 μl of normal human plasma. The cross-reactivity of the 6-hydroxy-zoxazolamine and chlorzoxazone was calculated at 50% displacement of the radioligand under the previously outlined conditions.

Results

After the first monthly booster injections (i.v. and s.c.), antibodies were detected in the serum from all four rabbits. However, a maximum titer was not reached until after the third booster injection. Rabbit No. 97 showed the highest titer with 50% binding of the $^3$H-zoxazolamine at a final dilution of 1:1250. Non-specific binding to control serum was 4% under the assay conditions and even in the presence of 50 μl of normal human plasma.

All of the data presented hereafter refer to the third lot of antiserum obtained from rabbit No. 97.

A calibration curve for zoxazolamine in the presence of 50 μl of normal human plasma was generated. The data was analyzed as outlined by Robard, Clin. Chem. 20, 1255 (1974) using a digital computer for iterative weighted linear regression analysis of logit B/Bo versus 1 n of the concentration of zoxazolamine. B and Bo are the amounts of antibody-bound $^3$H-zoxazolamine in the presence and absence of unlabelled drug, respectively. Both B and Bo were corrected for non-specific binding.

The calibration curve shows a linear response from 0.4 to 20 ng of added zoxazolamine with a slope of 1.09 and a correlation coefficient of 0.996.

The cross-reactivity of 6-hydroxy-zoxazolamine and chlorzoxazone was 1.5 and 0.16%, respectively.

I claim:

1. An immunogen composition comprising the diazoconjugate of 4-amino-N-(5-chloro-2-benzoxazolyl)benzamide and an immunogenic carrier material.

2. The composition of claim 1 wherein said immunogenic carrier material is bovine serum albumin.

3. An antibody specific to zoxazolamine prepared by innoculating a host animal with the antigen of claim 1 and collecting the serum from said host animal.

4. A method for the assay of zoxazolamine in a sample, which method comprises mixing said sample with a known amount of a labelled zoxazolamine compound and an antibody of claim 3 which will selectively complex with said zoxazolamine, measuring the degree of binding of the said labelled zoxazolamine compound and determining the amount of zoxazolamine present in said sample by comparing said degree of binding to a standard curve obtained by mixing known amounts of zoxazolamine with fixed amounts of said labelled zoxazolamine compound and determining the degree of binding for each known amount of said zoxazolamine.

5. The method of claim 4 wherein radiolabelled zoxazolamine is used.

6. The method of claim 5 wherein said radiolabelled zoxazolamine compound is $^3$H-zoxazolamine.

* * * * *